United States Patent [19]
Hanson et al.

[11] Patent Number: 5,246,959
[45] Date of Patent: Sep. 21, 1993

[54] POLY(AMINOALKYL)AMINOCARBONYL AMINOACYL AMINODIOL AMINO ACID DERIVATIVES AS ANTI-HYPERTENSIVE AGENTS

[75] Inventors: Gunnar J. Hanson, Skokie; John S. Baran, Winnetka, both of Ill.

[73] Assignee: G. D. Searle & Co., Chicago, Ill.

[21] Appl. No.: 807,700

[22] Filed: Dec. 16, 1991

Related U.S. Application Data

[63] Continuation of Ser. No. 370,963, Jun. 26, 1989, abandoned, which is a continuation-in-part of Ser. No. 214,700, Jul. 1, 1988, Pat. No. 4,900,745.

[51] Int. Cl.$^5$ .................. A61K 31/415; A61K 31/16; C07C 233/35; C07D 233/64
[52] U.S. Cl. ..................... 514/400; 514/19; 514/489; 514/616; 548/340.1; 560/25; 560/27; 560/125; 564/153
[58] Field of Search ............ 548/344, 340.1; 514/400, 19, 489, 616; 560/25, 27, 125; 564/153

[56] References Cited

U.S. PATENT DOCUMENTS 4,680,284 7/1987 Luly et al. ..................... 564/153
4,880,781 11/1989 Hester, Jr. et al. ............. 548/344

(List continued on next page.)

FOREIGN PATENT DOCUMENTS 128762 6/1984 European Pat. Off.

(List continued on next page.)

OTHER PUBLICATIONS

Umezawa et al, in *J. Antibiot.* (Tokyo), 23:259-262 (1970).

(List continued on next page.)

*Primary Examiner*—Robert W. Ramsuer
*Assistant Examiner*—MarySusan H. Gabilan
*Attorney, Agent, or Firm*—J. Timothy Keane

[57] ABSTRACT

Non-peptidyl compounds characterized generally as poly(aminoalkyl)aminocarbonyl aminoacyl aminodiol derivatives of amino acids are useful as renin inhibitors for the treatment of hypertension. Compounds of particular interest are of the formula

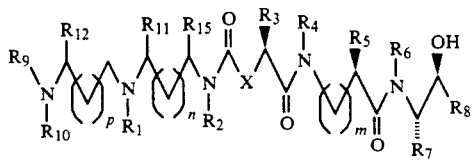

wherein X is selected from oxygen atom and methylene; wherein each of $R_9$ and $R_{10}$ is independently selected from hydrido, ethyl and methyl; wherein $R_9$ and $R_{10}$ may be taken together to form a heterocyclic ring having five or six ring atoms and containing one or two nitrogen atoms as ring atoms; wherein each of $R_1$ and $R_2$ is independently selected from hydrido, methyl, ethyl and isopropyl; wherein $R_3$ is selected from benzyl, phenethyl, pyridylmethyl and 2-pyridylethyl; wherein each of $R_4$ and $R_6$ is hydrido; wherein $R_7$ is cyclohexylmethyl; wherein $R_8$ is selected from

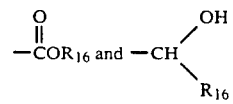

with the carbon bearing the hydroxyl radical being in the S configuration; wherein $R_{16}$ is selected from isopropyl, n-propyl, n-butyl and isobutyl; wherein each of $R_{11}$, $R_{12}$, $R_{14}$ and $R_{15}$ is hydrido; wherein m is zero or one and each of n and p is a number independently selected from zero through three; or a pharmaceutically-acceptable salt thereof; with the proviso that where m is zero, then $R_5$ is selected from imidazolemethyl, thiazolemethyl and isobutyl; and with the further proviso that when m is one, then $R_5$ is methyl or ethyl.

21 Claims, No Drawings

U.S. PATENT DOCUMENTS

| | | | |
|---|---|---|---|
| 4,900,745 | 2/1990 | Hanson et al. | 548/338.1 |
| 4,963,530 | 10/1990 | Hemmi et al. | 548/344 |
| 5,032,577 | 7/1991 | Fung et al. | 548/344 |
| 5,089,471 | 2/1992 | Hanson et al. | 564/153 |

FOREIGN PATENT DOCUMENTS

| | | |
|---|---|---|
| 172346A | 6/1985 | European Pat. Off. |
| 172347A | 6/1985 | European Pat. Off. |
| 181110 | 10/1985 | European Pat. Off. |
| 189203 | 1/1986 | European Pat. Off. |
| 200406 | 4/1986 | European Pat. Off. |
| 216539 | 9/1986 | European Pat. Off. |
| 229667 | 1/1987 | European Pat. Off. |
| 300189 | 6/1988 | European Pat. Off. |
| 307837 | 9/1988 | European Pat. Off. |
| 87/04349 | 7/1987 | PCT Int'l Appl. |

OTHER PUBLICATIONS

Gross et al, Science, 175, 656 (1971).
Boger, et al, *Nature,* 303, 81 (1983).
Kokubu et al, *Biochim. Biophys. Res. Commun.,* 118, 929 (1984).
Castro et al, *FEBS Lett.,* 167, 273 (1984).
Hanson et al, *Biochm. Biophys. Res. Comm.,* 132:155–161 (1985), 146:959–963 (1987).
Marshall, *Federation Proc.,* 35: 2494–2501 (1976).
Burton et al, Proc. Natl. Acad. Sci. USA, 77: 5476–5479 (1980).
Suketa et al, *Biochemistry,* 14: 3188 (1975).
Swales, *Pharmac. Ther.,* 7: 173–201 (1979).
Kokubu et al, *Nature,* 217: 456–457 (1968).
Matsushita et al, *J. Antibiotics,* 28: 1016–1018 (1975).
Lazar et al, *Biochem. Pharma.,* 23: 2776–2778 (1974).
Miller et al, *Biochem. Pharma.,* 21: 2941–2944 (1972).
Haber, *Clinical Science,* 59: 7s–19s (1980).
Rich et al, *J. Org. Chem.,* 43: 3624 (1978).
Rich et al, *J. Med. Chem.,* 23: 27 (1980).
Haber, Clin. and Exper. Hyper., A5(7&8), 1193 (1983).
Hanson et al., Biochem. and Biophys. Res. Comm., vol. 146, No. 3, 1987, pp. 959–963.
Hanson et al., Biochem. and Biophys. Res. Comm., vol. 132, No. 1, 1985, pp. 155–161.
Bolis et al., J. Med. Chem. 1987, 30, pp. 1729–1737.

POLY(AMINOALKYL)AMINOCARBONYL AMINOACYL AMINODIOL AMINO ACID DERIVATIVES AS ANTI-HYPERTENSIVE AGENTS

This application is a continuation of U.S. application Ser. No. 07/370,963 filed Jun. 26, 1989, now abandoned, which is a continuation-in-part of U.S. application Ser. No. 07/214,700 filed Jul. 1, 1988, now U.S. Pat. No. 4,900,745.

FIELD OF THE INVENTION

Renin-inhibiting compounds are known for control of hypertension. Of particular interest herein are non-peptidyl compounds useful as renin inhibiting agents.

BACKGROUND OF THE INVENTION

Renin is a proteolytic enzyme produced and secreted into the bloodstream by the juxtaglomerular cells of the kidney. In the bloodstream, renin cleaves a peptide bond in the serum protein angioten-sinogen to produce a decapeptide known as angiotensin I. A second enzyme known as angiotensin converting enzyme, cleaves angiotensin I to produce the octapeptide known as angiotensin II. Angiotensin II is a potent pressor agent responsible for vasoconstriction and elevation of cardiovascular pressure. Attempts have been made to control hypertension by blocking the action of renin or by blocking the formation of angiotensin II in the body with inhibitors of angiotensin I converting enzyme.

Classes of compounds published as inhibitors of the action of renin on angiotensinogen include renin antibodies, pepstatin and its analogs, phospholipids, angiotensinogen analogs, pro-renin related analogs and peptide aldehydes.

A peptide isolated from actinomyces has been reported as an inhibitor of aspartyl proteases such as pepsin, cathepsin D and renin [Umezawa et al, in *J. Antibiot. (Tokyo)*, 23, 259–262 (1970)]. This peptide, known as pepstatin, was found to reduce blood pressure in vivo after the the injection of hog renin into nephrectomized rats [Gross et al, *Science*, 175, 656 (1971)]. Pepstatin has the disadvantages of low solubility and of inhibiting acid proteases in addition to renin. Modified pepstatins have been synthesized in an attempt to increase the specificity for human renin over other physiologically important enzymes. While some degree of specificity has been achieved, this approach has led to rather high molecular weight hepta- and octapeptides [Boger et al, *Nature*, 303, 81 (1983)]; high molecular weight peptides are generally considered undesirable as drugs because gastrointestinal absorption is impaired and plasma stability is compromised.

Short peptide aldehydes have been reported as renin inhibitors [Kokubu et al, *Biochim. Biophys. Res. Commun.*, 118, 929 (1984); Castro et al, *FEBS Lett.*, 167, 273 (1984)]. Such compounds have a reactive C-terminal aldehyde group and would likely be unstable in vivo.

Other peptidyl compounds have been described as renin inhibitors. EP Appl. #128,762, published 18 Dec. 1984, describes dipeptide and tripeptide glycol-containing compounds as renin inhibitors [also see Hanson et al, *Biochm. Biophys. Res. Comm.*, 132, 155–161 (1985), 146, 959–963 (1987)]. EP Appl. #181,110, published 14 May 1986, describes dipeptide histidine derivatives as renin inhibitors. EP Appl. #189,203, published 30 Jul. 1986, describes peptidylaminodiols as renin inhibitors. EP Appl. #200,406, published 10 Dec. 1986, describes alkylnaphthylmethylpropionyl-histidyl aminohydroxy alkanoates as renin inhibitors. EP Appl. #216,539, published 1 Apr. 1987, describes alkylnaphthylmethylpropionyl published 22 Jul. 1987, describes acyl α-aminoacyl aminoacyl aminoalkanoate compounds as renin inhibitors orally administered for treatment of renin-associated hypertension. EP Appl. #229,667, aminodiol compounds having a piperazinylcarbonyl or an alkylaminoalkylcarbonyl terminal group at the N-amino acid terminus, such as 2(S)-{(1-piperazinyl)carbonyl]oxy]-3-phenylpropionyl}-Phe-His amide of 2(S)-amino-1-cyclohexyl-3(R),4(S)-dihydroxy-6-methylheptane. PCT Application No. WO 87/04349, published 30 Jul. 1987, describes aminocarbonyl aminoacyl hydroxyether derivatives having an alkylamino-containing terminal substitutent and which are described as having renin-inhibiting activity for use in treating hypertension. EP Appl. #300,189 published 25 Jan. 1989 describes amino acid monohydric derivatives having an alkylaminoalkylamino N-terminus mentioned as useful in treating hypertension.

For other articles describing previous efforts to devise renin inhibitors, see Marshall, *Federation Proc.*, 35, 2494–2501 (1976); Burton et al, *Proc. Natl. Acad. Sci. USA*, 77, 5476–5479 (1980); Suketa et al, *Biochemistry*, 14, 3188 (1975); Swales, *Pharmac. Ther.*, 7, 173–201 (1979); Kokubu et al, *Nature*, 217, 456–457 (1986); Matsushita et al, *J. Antibiotics*, 28, 1016–1018 (1975); Lazar et al, *Biochem. Pharma.*, 23, 2776–2778 (1974); Miller et al , *Biochem. Pharma.*, 21, 2941–2944 (1972); Haber, *Clinical Science*, 59, 7s-19s (1980); Rich et al, *J. Org. Chem.*, 43, 3624 (1978); *J. Med. Chem.*, 23, 27 (1980); especially Haber, *Clin. and Exper. Hyper.*, A5(7&8), 1193 (1983); and European Patent Applications #172,346 and #172,347 published 26 Feb. 1986.

DESCRIPTION OF THE INVENTION

Non-peptidyl poly(aminoalkyl)aminocarbonyl aminoacyl aminodiol amino acid derivatives having utility as renin inhibitors for treatment of hypertension in mammals constitute a family of compounds of general Formula I:

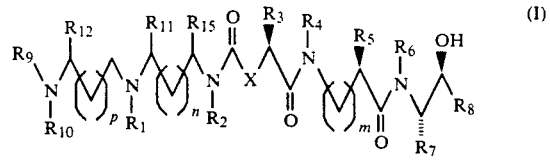

wherein X is selected from oxygen atom, methylene and $>NR_{13}$ with $R_{13}$ selected from hydrido, alkyl and benzyl; where of $R_9$ and $R_{10}$ is a group independently selected from hydrido, alkyl, cycloalkyl, alkoxycarbonyl, benzyloxycarbonyl, loweralkanoyl, alkylaminoalkyl, dialkylaminoalkyl, aminoalkyl, alkylaminoalkylaminoalkyl, haloalkylacyl, phenyl, benzyl, heterocyclicalkyl, naphthyl and naphthylmethyl, any one of which groups having a substitutable position may be optionally substituted with one or more radicals selected from alkyl, alkoxy, alkenyl, alkynyl, halo, haloalkyl, cyano and phenyl; wherein $R_9$ and $R_{10}$ may be taken together to form a heterocyclic ring having one or two hetero atoms as ring atoms selected from nitrogen, oxygen and sulfur, which heterocyclic ring has 4 to 10 ring members and contains as a ring member the nitrogen atom of Formula I to which $R_9$ and $R_{10}$ are attached; and wherein each wherein each of $R_1$ and $R_2$ is independently selected from hydrido, alkyl, alkylaminoalkyl, dialkylaminoalkyl, alkylacylaminoalkyl, benzyl and cycloalkyl; wherein $R_3$ is selected from alkyl, acyaminoalkyl, phenylalkyl, naphthylmethyl, cycloalkylalkyl, aryl and heterocyclicalkyl, wherein the aromatic portion of any of said phenylalkyl, naphthylmethyl, aryl and heterocyclicalkyl may be substituted by one or more halo or akyl or by both; wherein each of $R_4$ and $R_6$ is independently selected from hydrido, alkyl, benzyl and cycloalkyl; wherein $R_7$ is selected from substituted or unsubstituted cycloalkyl, phenyl, cycloalkylalkyl and phenylalkyl, any one of which may be substituted with one or more groups selected from alkyl, alkoxy, halo, haloalkyl, alkenyl, alkynyl and cyano; wherein $R_8$ is selected from hydrido, alkyl, haloalkyl, alkylcycloalkyl, alkylcycloalkenyl, alkoxycarbonyl,

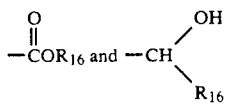

with the carbon bearing the hydroxyl radical being in the S configuration; wherein $R_{16}$ is selected from hydrido, alkyl, haloalkyl, alkylcycloalkyl, alkylcycloalkenyl and alkoxycarbonyl; wherein each of $R_{11}$, $R_{12}$, $R_{14}$ and $R_{15}$ is independently selected from hydrido, alkyl, alkylaminoalkyl and phenyl; and wherein m is zero or one and each of n and p is a number independently selected from zero through five; or a pharmaceutically-acceptable salt thereof;

with the proviso that where m is zero, then $R_5$ is selected from hydrido, alkyl, benzyl, cycloalkyl, cycloalkylalkyl, hydroxyalkyl, alkoxyalkyl, alkylthioalkyl, heterocyclicalkyl, sulfonylheterocyclicalkyl and acylheterocyclicalkyl; and with the further proviso that when m is one, then $R_5$ is selected from hydrido, alkyl, benzyl, cycloalkyl, cycloalkylalkyl, alkoxyalkyl, alkylthioalkyl and imidazolemethyl.

Two distinct families of renin-inhibiting compounds are specified within Formula I, namely, those families being defined by the values of m. A first family of compounds consists of those α-amino acid derivatives defined by the condition where m is zero. A second family of compounds consists of those β-amino acid derivatives defined by the condition where m is one.

A preferred family of compounds consists of those compounds of Formula I wherein X is selected from oxygen atom, methylene and $>NR_{13}$ with $R_{13}$ selected from hydrido, alkyl and benzyl; wherein each of $R_9$ and $R_{10}$ is a group independently selected from hydrido, loweralkyl, cycloalkyl, alkoxycarbonyl, loweralkanoyl, benzyloxycarbonyl, dialkylaminoalkyl, phenyl, benzyl, heterocyclicalkyl, naphthyl and naphthylmethyl, any one of which groups having a substitutable position may be optionally substituted with one or more radicals selected from alkyl, alkoxy, alkenyl, alkynyl, halo, haloalkyl, cyano and phenyl; wherein $R_9$ and $R_{10}$ may be taken together to form a heterocyclic ring having 5 to 7 ring members and one or two nitrogen atoms as ring atoms; wherein each of $R_1$, $R_2$, $R_4$ and $R_6$ is independently selected from hydrido and alkyl; wherein $R_3$ is selected from phenylalkyl, cyclohexylmethyl, naphthylmethyl, pyridylmethyl, pyridylethyl and pyridylpropyl; wherein $R_7$ is selected from substituted or unsubstituted cyclohexylmethyl and benzyl, either one of which may be substituted with one or more groups selected from alkyl, alkoxy, halo and haloalkyl; wherein $R_8$ is selected from hydrido, ethyl, n-propyl, n-buty, isobutyl, isoamyl, fluoroalkyl,

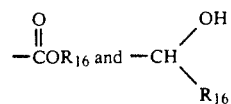

with the carbon bearing the hydroxyl radical being in the S configuration; wherein $R_{16}$ is selected from hydrido, ethyl, n-propyl, isopropyl, n-butyl, isobutyl and fluoroalkyl; wherein each of $R_{11}$, $R_{14}$, $R_{15}$ and $R_{12}$ is independently selected from hydrido and lower alkyl; wherein m is zero or one and each of n and p is a number independently selected from zero through five; or a pharmaceutically-acceptable salt thereof;

with the proviso that where m is zero, then $R_5$ is selected from hydrido, alkyl, benzyl, cycloalkyl, cycloalkylalkyl, imidazolemethyl, imidazoleethyl, thiazolemethyl, pyridylmethyl, sulfonylimidazolemethyl and acylimidazolemethyl; and with the further proviso that when m is one, then $R_5$ is selected from hydrido, alkyl and imidazolemethyl.

A further preferred family of compounds consists of those compounds of Formula I wherein X is selected from oxygen atom, methylene and $>NR_{13}$ with $R_{13}$ selected from hydrido, alkyl and benzyl; wherein each of $R_9$ and $R_{10}$ is independently selected from hydrido, dialkylaminoalkyl, lower alkyl, alkoxycarbonyl, heterocyclicalkyl and benzyl; wherein $R_9$ and $R_{10}$ may be taken together to form a heterocyclic ring having five or six ring members and one or two nitrogen atoms as ring atoms; wherein each of $R_1$, $R_2$, $R_4$ and $R_6$ is independently selected from hydrido and alkyl; wherein $R_3$ is selected from benzyl, phenethyl, cyclohexylmethyl, phenpropyl, pyridylmethyl, 2-pyridylethyl and 3-pyridylpropyl; wherein $R_7$ is cyclohexylmethyl; wherein $R_8$ is selected from

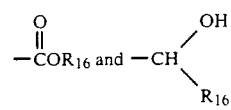

with the carbon bearing the hydroxyl radical being in the S configuration; wherein $R_{16}$ is selected from hydrido, ethyl, n-propyl, isopropyl, n-butyl and isobutyl; wherein each of $R_{11}$, $R_{14}$, $R_{15}$ and $R_{12}$ is independently selected from hydrido and methyl; wherein m is zero or one and each of n and p is a number independently selected from zero through five; or a pharmaceutically-acceptable salt thereof;

with the proviso that where m is zero, then $R_5$ is selected from isobutyl, imidazolemethyl, imidazoleethyl, thiazolemethyl and pyridylmethyl; and with the further proviso that when m is one, then $R_5$ is methyl or ethyl.

A more preferred family of compounds consists of those compounds of Formula I wherein X is selected from oxygen atom, methylene and $>NR_{13}$ with $R_{13}$ selected from hydrido and methyl; wherein each of $R_9$ and $R_{10}$ is independently selected from hydrido, loweralkyl, alkoxycarbonyl, heterocyclicalkyl and benzyl; wherein $R_9$ and $R_{10}$ may be taken together to form a heterocyclic ring having five or six ring atoms and containing one or two nitrogen atoms as ring atoms; wherein each of $R_1$, $R_2$, $R_4$ and $R_6$ is independently selected from hydrido and alkyl; wherein $R_3$ is selected from benzyl, phenethyl, cyclohexylmethyl, pyridylmethyl, 2-pyridylethyl, and 3-pyridylpropyl; wherein $R_7$ is cyclohexylmethyl; wherein $R_8$ is selected from

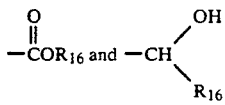

with the carbon bearing the hydroxyl radical being in the S configuration; wherein $R_{16}$ is selected from isopropyl, n-propyl, n-butyl and isobutyl; wherein each of $R_{11}$, $R_{12}$, $R_{14}$ and $R_{15}$ is independently selected from hydrido and methyl; wherein m is zero or one and each of n and p is a number independently selected from zero through three; or a pharmaceutically-acceptable salt thereof; with the proviso that where m is zero, then $R_5$ is selected from isobutyl, imidazolemethyl, imidazoleethyl, thiazolemethyl and pyridylmethyl; and with the further proviso that when m is one, then $R_5$ is methyl or ethyl.

A particularly preferred family of compounds consists of those compounds of Formula I wherein X is selected from oxygen atom and methylene; wherein each of $R_9$ and $R_{10}$ is independently selected from hydrido, methyl, ethyl, 2-(1H-imidazole-2-yl)ethyl and t-butyloxycarbonyl; wherein $R_9$ and $R_{10}$ may be taken together to form a heterocyclic ring having five or six ring atoms and containing one or two nitrogen atoms as ring atoms; wherein each of $R_1$ and $R_2$ is independently selected from hydrido, methyl, ethyl and isopropyl; wherein $R_3$ is selected from benzyl, phenethyl, cyclohexylmethyl, pyridylmethyl and 2-pyridylethyl; wherein each of $R_4$ and $R_6$ is hydrido; wherein $R_7$ is cyclohexylmethyl; wherein $R_8$ is selected from

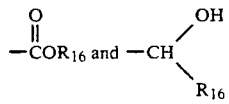

with the carbon bearing the hydroxyl radical being in the S configuration; wherein $R_{16}$ is selected from isopropyl, n-propyl, n-butyl and isobutyl; wherein each of $R_{11}$, $R_{12}$, $R_{14}$ and $R_{15}$ is hydrido; wherein m is zero or one and each of n and p is a number independently selected from zero through three; or a pharmaceutically-acceptable salt thereof; with the proviso that where m is zero, then $R_5$ is selected from imidazolemethyl, thiazolemethyl and isobutyl; and with the further proviso that when m is one, then $R_5$ is methyl or ethyl.

A more particularly preferred family of compounds consists of those compounds of Formula I wherein X is selected from oxygen atom and methylene; wherein each of $R_9$ and $R_{10}$ is a group independently selected from hydrido, methyl, ethyl, 2-(1H-imidazole-2-yl)ethyl and t-butyloxycarbonyl; wherein each of $R_1$ and $R_2$ is independently selected from hydrido, methyl, ethyl and isopropyl; wherein $R_3$ is selected from cyclohexylmethyl, benzyl, phenethyl, pyridylmethyl and 2-pyridylethyl; wherein each of $R_4$ and $R_6$ is hydrido; wherein $R_7$ is cyclohexylmethyl; wherein $R_8$ is isoproxycarbonyl or 3-methylbut-1-ol; wherein $R_9$ and $R_{10}$ may be taken together to form a heterocyclic ring having five or six ring atoms and containing one or two nitrogen atoms as ring atoms; wherein each of $R_{11}$, $R_{12}$, $R_{14}$ and $R_{15}$ is hydrido; wherein m is zero or one and each of n and p is a number independently selected from zero through three; or a pharmaceutically-acceptable salt thereof; with the proviso that where m is zero, then $R_5$ is selected from imidazolemethyl and isobutyl; and with the further proviso that when m is one, then $R_5$ is methyl or ethyl.

A most preferred family of compounds of Formula I consists of the following compounds:

O-{N-[2-{N-[2-(N,N-dimethylamino)ethyl]-N-methylamino}-ethyl]-N-methylaminocarbonyl}-3-L-phenyllactyl-L-histidineamide of (2S,3R,4S)-2-amino-1-cyclohexyl-3,4-dihydroxy-6-methylheptane;

O-{N-[2-{N-[2-(N,N-dimethylamino)ethyl]-N-methylamino}-ethyl]-N-methylaminocarbonyl}-3-L-phenyllactyl-L-leucineamide of (2S,3R,4S)-2-amino-1-cyclohexyl-3,4-dihydroxy-6-methylheptane;

O-{N-[2-{N-[2-(N,N-dimethylamino)ethyl]-N-methylamino}-ethyl]-N-methylaminocarbonyl}-3-L-phenyllactyl-α-(R)-methyl-β-alanineamide of (2S,3R,4S)-2-amino-1-cyclohexyl-3,4-dihydroxy-6-methylheptane;

O-{N-[2-{N-[2-(N,N-dimethylamino)ethyl]-N-methylamino}-ethyl-N-methylaminocarbonyl}-3-L-homophenyllactyl-α-(R)-methyl-β-alanineamide of (2S,3R,4S)-2-amino-1-cyclohexyl-3,4-dihydroxy-6-methylheptane;

O-{N-[2-{N-[2-(N,N-dimethylamino)ethyl]-N-methylamino}-ethyl]-N-methylaminocarbonyl}-3-L-homophenyllactyl-α-(R)-ethyl-β-alanineamide of (2S,3R,4S)-2-amino-1-cyclohexyl-3,4-dihydroxy-6-methylheptane; and 3-{N-[2-(N,N-dimethylamino)ethyl]-N-methylamino}ethyl]-N-methylaminocarbonyl}-2-(R)-(2-phenylethyl)-propionyl-α-(R)-ethyl-β-alanineamide of (2S,3R,4S)-2-amino-1-cyclohexyl-3,4-dihydroxy-6-methylheptane.

Unless otherwise described, the chemical groups recited herein shall have meanings as follows: "alkyl" includes linear and branched radicals; "lower alkyl" means alkyl radicals containing one to about 10 carbon atoms in a linear or branched configuration, examples of which include methyl, ethyl, n-propyl, isopropyl, n-butyl, sec-butyl, iso-butyl, tert-butyl, n-pentyl, neopentyl, n-hexyl, 1-methylhexyl, n-heptyl, 2-ethylheptyl, n-octyl, 3-propyloctyl, n-nonyl, 4-butylnonyl, n-decyl and the like. "Haloalkyl" means alkyl radicals substituted at one or more substitutable positions with one or more halo groups. Preferred haloalkyl group are those provided by lower alkyl radicals substituted at least at one position with one, two or three halo groups such as fluoro or chloro, a specific example of which is trifluoromethyl. "Alkylcycloalkyl" means a cyclized alkyl having from four to about nine ring carbon atoms, any one or more of the substitutable ring carbon atoms being substituted with an alkyl group, preferably a lower alkyl group. "Alkoxycarbonyl" means an oxycarbonyl radical having an alkyl, preferably lower alkyl, group attached to the oxygen atom. "Aryl" means an aromatic hydrocarbon radical provided by a homocyclic or heterocyclic ring system, such as phenyl, naphthyl, and pyridyl. "Acyl" means a carbonyl radical attached to a hydrocarbon moiety, typically an alkyl or lower alkyl group. "Heterocyclicalkyl" means a cyclized group having three to about ten ring members, of which one to about three of such ring members is a hetero atom selected from oxygen, nitrogen and sulfur, with the remaining ring members being carbon atoms and such cyclized group being fully unsaturated, or partially saturated, or fully saturated, and having an alkyl group attached to any ring member of the heterocyclic ring, through which alkyl group the heterocyclic ring is attached to the Formula I backbone. Examples of heterocyclicalkyl are imidazolemethyl, 2-imidazoleethyl, pyrimidinemethyl, 2-pyrimidineethyl, pyridylmethy and 2-pyridylethyl. The term "imidazolemethyl" includes, for example, radicals where the methyl fragment, through which the heterocyclic ring is attached to the Formula 1 backbone, is attached to any ring member (nitrogen or carbon) of the heterocyclic ring.

Based upon the foregoing, the meanings of the following terms should be readily discernible, namely, "acylaminoalkyl", "cycloalkyl", "cycloalkylalkyl", "phenylalkyl" and "alkoxy".

Compounds of Formula I have at least five asymmetric carbons. Such compounds whether in their pure form or as diastereomeric mixtures are embraced in the Formula I compounds of the invention. Many of the more active renin inhibitors are provided by compounds having a specific arrangement of stereogenic carbons. Within Formula I, reading from the N terminus to the C terminus (terminating with the diol moiety), the preferred configurations for the asymmetric carbons are as follows:

sideration of a variety of factors, including the type, age, weight, sex, and medical condition of the patient, the severity of the hypertension, the route of administration, and the particular compound employed. Dosages of the compounds are ordinarily in the range from about 0.5 to about 100 mg/kg (active compound-to-body weight), and preferably from about 1.0 to about 20 mg/kg given orally or by injection.

Compounds of Formula I are also useful as diagnostic agents for identification of hypertension due to renin excess.

Compounds of Formula I can be administered as prodrugs. Preferably, esterification of one or more of the hydroxyl groups of the compounds of Formula I is accomplished with amino acids to make aminoesters, succinates to make succinic acid esters, alkanoic acids to make carboxylic acid esters such as valerates, or phosphates to make phosphoric acid esters. Aminoesters and valerates of the Formula I compounds are more preferred.

Procedures for preparation of compounds of Formula I are set forth in the schemes and descriptions under General Synthetic Schemes I & II taken with the specific procedures described in Examples 1–13 which follow thereafter. The substituents X and $R_1$ through $R_{15}$ are as described above for the Formula I substituents.

GENERAL SYNTHETIC SCHEMES I & II

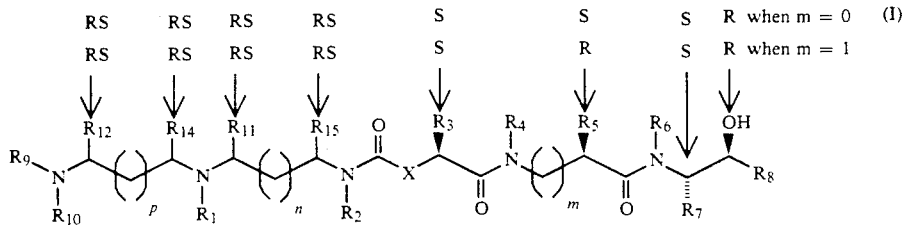

Compounds of Formula I have been found to inhibit renin and thus limit the production of angiotensin I which, in turn, limits the production of angiotensin II in mammals. Angiotensin II is a potent vasoconstrictor and participates in the formation of aldosterone which regulates sodium and water balance in mammals. Thus, compounds of Formula I are therapeutically useful in methods for treating hypertension by administering to a hypertensive patient a therapeutically-effective amount of a compound of Formula I. The phrase "hypertensive patient" means, in this context, a mammalian subject suffering from the effects of hypertension or susceptible to hypertensive conditions if not treated to prevent or control such hypertension.

These compounds can be formulated into pharmaceutically-acceptable dosage forms by any of a number of well-known carriers or diluents. The compounds can be formulated using pharmacologically-acceptable acid addition salts and can be used in a suitable hydrated form. The formulated compounds can be administered in oral dosage forms such as tablets, capsules, pills, powders, or granules. The compounds can also be administered intramuscularly, using forms known to the pharmaceutical art. In general, the preferred form of administration is oral. A therapeutically effective but non-toxic quantity of the compound is employed in treatment of high blood pressure in mammals. The dosage regimen for preventing or treating hypertension with the compounds of Formula I is selected upon con- A suitably protected amino aldehyde 1 (Scheme I) is treated with a Grignard reagent, preferably vinylmagnesium bromide to obtain vinyl carbinol 2. This material, suitably protected, is oxidized, preferably with ozone, followed by dimethyl sulfide treatment to give 3. Aldehyde 3 is reacted with an organometallic reagent such as isobutylmagnesium chloride to give compound 4, or alternatively this aldehyde is oxidized with Jones reagent and the resulting acid is esterified to give compound 4. Alternatively, the oxidation may be carried out with Jones reagent to give the corresponding carboxylic acid. The acid is then esterified and this product is further reacted in the same manner as compound 4.

This intermediate 4 is deprotected and then coupled using standard amide/peptide coupling methodology, to either alpha or beta amino acid derivatives, suitably protected, to give compound 5. This intermediate is deprotected and then coupled using standard amide/peptide coupling methodology to intermediate 9 (shown in Scheme II) to give renin inhibitor of Formula I. Synthetic Scheme II shows synthetic routes to intermediate 9, using the reaction of intermediates 7 and 8 followed by deprotection ($R_{10}$ and $R_1$ may be removable N-protecting groups such as tertbutoxycarbonyl). The synthesis of various types of intermediates 8 (shown more explicitly as intermediates 11, 13 and 15) is depicted, depending on whether X is O, $CH_2$ or $NHR_{13}$.

If X=O, a suitably protected lactic acid derivative is treated with phosgene or carbonyl diimidazole to give intermediate 11. If X=CH₂, a suitably protected succinic acid derivative is activated by treatment with base/isobutylchloroformate or other standard activating agent to give intermediate 13. If X=NHR₁₃, a suitably protected amino acid derivative is activated by treatment with phosgene or other activating agent to give intermediate 15.

Synthetic Scheme I

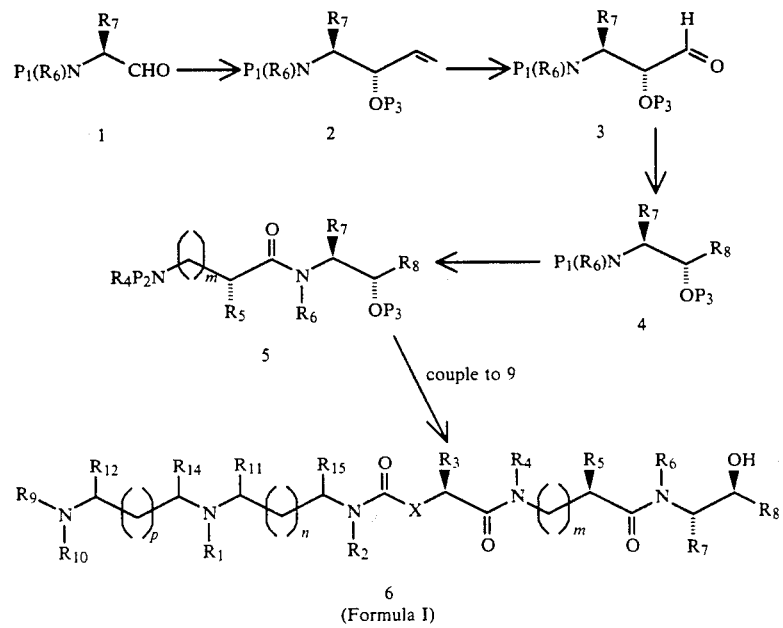

P₁ is and N-protecting group
P₂ is H or N-protecting group
P₃ is H or oxygen protecting group Synthetic Scheme II

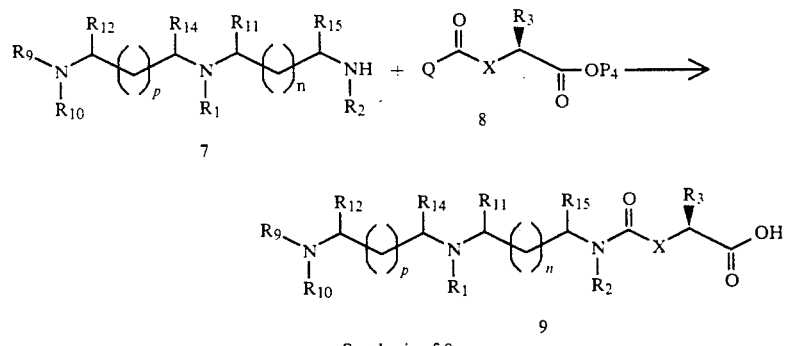

Synthesis of 8:

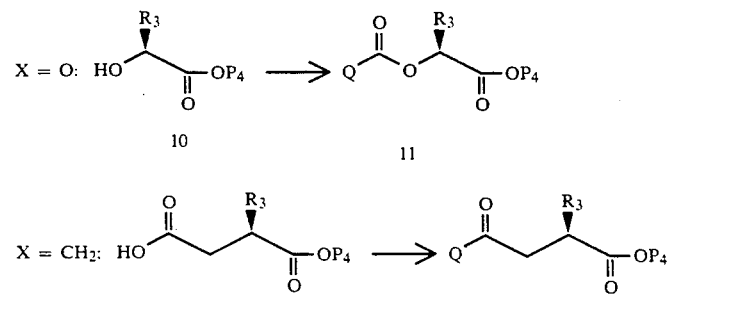

Q is an activating group such as Cl, imidazole P₄ is alkyl, benzyl, oxygen protecting group

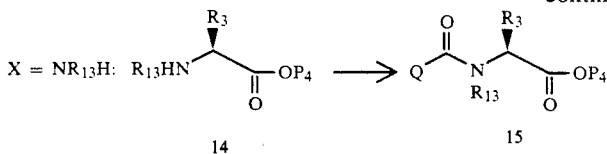

The following examples are provided to illustrate the present invention and are not intended to limit the scope thereof. Those skilled in the art will readily understand that known variations of the conditions and processes of the following preparative procedures can be used to prepare these compounds. All temperatures expressed are in degrees Centigrade. Within the foregoing synthetic description and examples which follow, abbreviations have meanings as indicated below:

| | |
|---|---|
| BOC = | t-butyloxycarbonyl |
| i-Bu = | isobutyl |
| Leu = | leucine |
| Ac = | acyl |
| Me = | methyl |
| TFA = | trifluoroacetic acid |
| THF = | tetrahydrofuran |
| im = | imidazole |

Example 1

(3S,4S)-N-[(tert-Butyloxy)carbonyl]-4-amino-3-acetoxy-5-phenylpentene

The preparation of the above intermediate was carried out using the procedure described in Hanson, et al., (1985) J. Org. Chem. 50, 5399.

Example 2

(2R,3S)-N-[(tert-Butyloxy)carbonyl]-3-amino-2-acetoxy-4-phenylbutanal

The preparation of the above intermediate was carried out as described in Hanson, et al. above. Ozone/oxygen was bubbled at −70° into a solution of 2.55 g (8.0 mmol) of the allylic acetate of Example 1 in 100 mL of methylene chloride until a deep blue color persisted. Oxygen was introduced until the blue color completely faded, then 3.0 mL of $Me_2S$ was added and the solution was allowed to warm to 0°-5° and stand overnight. The solvent was removed at 0° under vacuum yielding the title compound as a thick yellow oil which was used in the following step without purification.

Example 3

(2S,3R,4S)-N-[(tert-Butyloxy)carbonyl]-2-amino-1-phenyl-3,4-dihydroxy-6-methylheptane The oil prepared in Example 2 was dissolved under nitrogen in 100 mL of dry THF and cooled to −70°. To this solution was added 13 mL (26 mmol) of a 2.0M solution of isobutylmagnesium chloride in ether and the stirred mixture was allowed to warm to room temperature and stir for 2 hrs. After decomposition with $MeOH/H_2O$ the mixture was diluted with ether, washed with saturated $NH_4Cl$ solution twice, then dried and the solvents stripped off under vacuum. The residue was allowed to stand overnight in 80% MeOH-$H_2O$ containing excess ammonium hydroxide. The MeOH was stripped off and the mixture was extracted with ether. These extracts were combined, washed with water, dilute $KHSO_4$, then dried and evaporated to give 2.36 g of a yellow glass which crystallized from 50 mL of pentane on standing overnight. The yellow-white powder obtained was recrystallized from ether-hexane and furnished the title compound (0.41 g) as white, hairy needles, mp 134°-136°, Rf (ether): single spot, 0.6. By chromatography of the mother liquors and crystallization of the appropriate fractions, an additional 0.22 g of product, mp 138°-139°, was obtained. Anal: Calc'd. for $C_{19}H_{31}NO_4$ (337.45) C, 67.62; H, 9.26; N, 4.15. Found: C, 67.51; H, 9.43; N, 4.24.

Example 4

(2S,3R,4S)-N-(tert-Butyloxy)carbonyl]-2-amino-1-cyclohexyl-3,4-dihydroxy-6-methylheptane The diol of Example 3, 0.27 g, was reduced in MeOH with 60 psi $H_2$ at 60° in 3 hrs using 5% Rh/C catalyst. After filtering, the solvent was stripped off and the white crystals were recrystallized from $CH_2Cl_2$-hexane to furnish tiny needles of the title compound, 0.19 g, mp 126°-128°; further recrystallization gave mp 128.5°-129.5°. Rf (ether): single spot, 0.8. Anal: Calc'd. for $C_{19}H_{37}NO_4$ (343.50): C, 66.43; H, 10.86; N, 4.08. Found: C, 66.43; H, 11.01; N, 4.03.

Example 5

L-Leucineamide of (2S,3R,4S)-2-amino-1-cyclohexyl-3,4-dihydroxy-6-methylheptane

The title compound of Example 4 was treated with trifluoroacetic acid (TFA) for 30 minutes at room temperature and the solvent evaporated. The residue was neutralized with aqueous potassium carbonate and the free amine was extracted with ethyl acetate. This amine was then coupled to Boc-L-leucine-OH following the general procedure given in Example 6. The resulting amide was treated with TFA for 30 minutes at room temperature and the solvent evaporated. The residue was neutralized with aqueous potassium carbonate and the mixture extracted with ethyl acetate. After evaporation, the title free base was obtained: Rf=0.45 (single spot, 9:1 methylene chloride-MeOH, silica); 400 MHz NMR (DMSO) spectrum: consistent with structure. Anal: Calc'd. for $C_{20}H_{40}N_2O_3 + 0.5 H_2O$: C, 65.70; H, 11.31; N, 7.67. Found: C, 65.62; H, 11.01; N, 7.49.

Example 6

Boc-(im-Tosyl)-L-histidineamide of (2S,3R,4S)-2-amino-1-cyclohexyl-3,4-dihydroxy-6-methylheptane To a stirred solution of N-Boc-(im-tosyl)-L-histidine (809 mg, 1.6 eq) in methylene chloride(5 ml) cooled with an ice/salt bath was added N-methylpiperidine (0.240 ml, 1.6 eq) followed by isobutylchloroformate (0.224 ml, 1.4 eq). After 5 minutes, the free base (300 mg, 1.23 mmol), which had been previously formed by treating the title compound of Example 4 with trifluoroacetic acid followed by potassium carbonate as described in Example 5, dissolved in methylene chloride (5 mL) was added and the reaction mixture was stirred at 0° overnight ca. 15h. The methylene chloride was evaporated in vacuo to afford an oily residue which was partitioned between ethyl acetate and saturated sodium bicarbonate. The organic layer was separated and further washed with KHSO₄ solution (1M) followed by NaHCO₃ (1M). The ethyl acetate layer was dried (MgSO₄) and evaporated in vacuo to afford a white solid, which was recrystallized from methanol/diethyl ether. This gave the title compound; (560 mg, 72% yield), 300 MHz ¹H NMR was fully consistent with the proposed structure. Anal: Calc'd for $C_{32}H_{50}O_7N_4S + 0.75\ H_2O$: C, 59.28; H, 8.01; N, 8.64. Found: C, 59.31; H, 7.98; N, 8.63.

Example 7

(im-Tosyl)-L-histidineamide of (2S,3R,4S)-2-amino-1-cyclohexyl-3,4-dihydroxy-6-methylheptane To a stirred solution of the title compound of Example 6 (3.78 g, 5.96 mmol) in methylene chloride (20 mL) and methanol (5 mL) was added trifluoroacetic acid (25 mL). The reaction mixture was stirred at room temperature for 30 min and then poured onto saturated sodium bicarbonate solution. The solution was adjusted to pH > 12 by addition of potassium carbonate and then extracted with ethyl acetate. The organic extracts were dried (MgSO₄), and evaporated to afford a solid white residue. Recrystallization from methanol/diethyl ether gave the title compound; (2.8 g, 88% yield); 300 MHz ¹H NMR spectrum: consistent with the proposed structure. Anal: Calc'd. for $C_{27}H_{42}N_4O_5S + 0.7\ H_2O$: C, 59.25; H, 7.99; N, 10.24. Found: C, 59.29; H, 7.75; N, 10.15.

Example 8

N-Boc-α-(R)-methyl-β-alanineamide of (2S,3R,4S)-2-amino-1cyclohexyl-3,4-dihydroxy-6-methylheptane To a solution of N-Boc-α-(R,S)-methyl-β-alanine (137 mg, 0.67 mmol) in methylene chloride (4 mL) at −10° C. was added N-methylpiperidine (61 mg, 0.61 mmol) followed by isobutylchloroformate (75 mg, 0.55 mmol). After stirring for 5 min, a solution of (2S,3R,4S)-2-amino-1-cyclohexyl-3,4-dihydroxy-6-methylheptane (101 mg, 0.41 mmol) [prepared from the title compound of Example 4 by treatment with trifluoroacetic acid, followed by aqueous potassium carbonate]in methylene chloride (2 mL) was added. The resulting solution was stirred for 3 hours at −10° C., followed by 2 hours at room temperature at which time a white solid was isolated by filtration (60 mg, 34% yield): Rf=0.3 (5% MeOH/methylene chloride, silica gel); mp 197°-200°; 1H NMR (CDCl₃): consistent with proposed structure. Anal. calcd for $C_{23}H_{44}N_2O_5 + 0.25\ H_2O$: C,63.77; H,10.35; N,6.46. Found: C,63.84; H,10.50; N,6.45.

Example 9

α-(R)-Methyl-β-alanineamide of (2S,3R,4S)-2-amino-1-cyclohexyl-3,4-dihydroxy-6-methylheptane The title compound of Example 8 (53 mg, 0.12 mmol) was stirred with a mixture of trifluoroacetic acid and methanol (9:1, 5 mL). The resulting solution was allowed to stand at room temperature for 20 minutes, then the solvent was evaporated. The resulting oil was stirred for 2 hours with aqueous potassium carbonate (5%, 10 mL). This mixture was then extracted with ethyl acetate which was dried, filtered and evaporated to give the title compound (40 mg, 100%): Rf: 0.10 (5% MeOH/methylene chloride, silica gel). This material was used without further purification.

Example 10

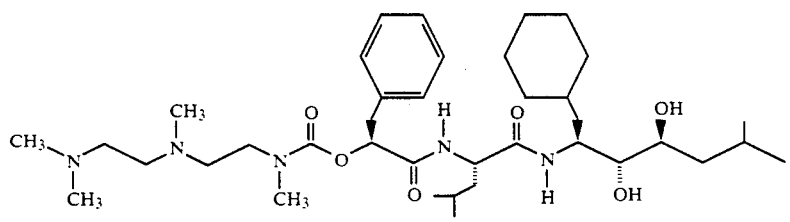

40

O-{N-2-{[2-(N N-dimethylamino)ethyl]-N-methylamino}-ethyl]-N-methylaminocarbonyl}-3-L-phenyllactyl-L-leucineamide of (2S,3R,4S)-2-amino-1-cyclohexyl-3,4-dihydroxy-6-methylheptane The title compound of Example 8 (500 mg) was dissolved in methylene chloride (3 mL) and cooled to 0°. Isobutylchloroformate (170 mg) was added and the mixture was stirred for 8 minutes. The title compound of Example 5 (430 mg) was then added and the mixture stirred at 0° for 3 hours and at a room temperature for 8 hours. The solvent was evaporated and the residue taken up in methanol (15 mL). To this solution was added 1N potassium hydroxide (2 mL) and the mixture was allowed to stand at room temperature for 15 minutes. The methanol was evaporated and the mixture partitioned between ethyl acetate and water. The organic layer was isolated, dried and evaporated to give the title compound as an oil (645 mg); 200 MHz'H NMR: consistent with proposed structure. Anal. calcd for $C_{38}H_{67}N_5O_6 + 1H_2O$: C,64.46; H, 9.82; N,9.89. Found: C,64.61; H,8.97; N,9.90.

Example 11

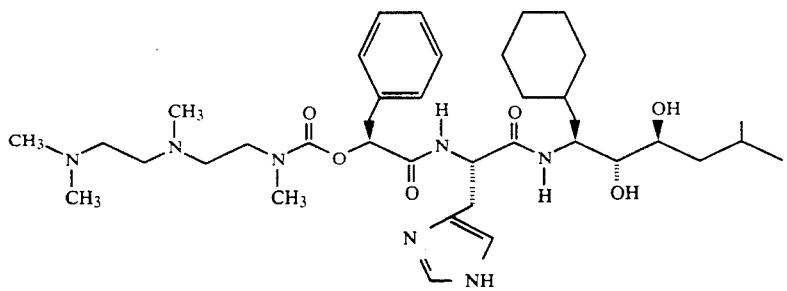

O-{N-[2-{N-[2-(N,N-dimethylamino)ethyl]-N-methylamino}-ethyl]-N-methylaminocarbonyl}-3-L-phenyllactyl-L-histidineamide of (2S,3R,4S)-2-amino-1-cyclohexyl-3,4-dihydroxy-6-methylheptane The procedure of Example 10 was used, substituting (im-Tosyl)-L-histidineamide of (2S,3R,4S)-2-amino-1-cyclohexyl-3,4-dihydroxy-6-methylheptane for L-leucineamide of (2S,3R,4S)-2-amino-1-cyclohexyl-3,4-dihydroxy-6-methylheptane (title compound of Example 5) to give the title compound as an oil; 200 MHz'H NMR: consistent with proposed structure.

Example 12

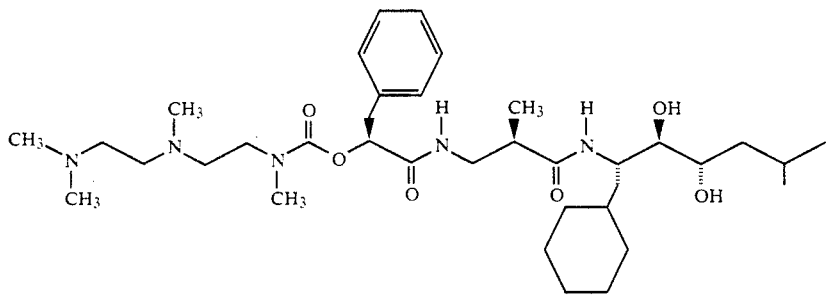

O-{N-[2-{N-[2-(N,N-dimethylamino)ethyl]-N-methylamino}-ethyl]-N-methylaminocarbonyl-3-L-phenyllactyl-α-(R)-methyl-β-alanineamide of (2S,3R,4S)-2-amino-1-cyclohexyl-3,4-dihydroxy-6-methylheptane The procedure of Example 10 was used, substituting α-(R)-Methyl-β-alanineamide of (2S,3R,4S)-2-amino-1-cyclohexyl-3,4-dihydroxy-6-methylheptane for L-leucineamide of (2S,3R,4S)-2-amino-1-cyclohexyl-3,4-dihydroxy-6-methylheptane (title compound of Example 5) to give the title compound as an oil; 200 MHz'H NMR: consistent with proposed structure. Anal. calcd for $C_{36}H_{63}N_5O_6 + 0.5$ $H_2O$: C,64.44; H,9.61; N,10.43. Found: C,64.44; H,9.16; N,10.05.

Example 13

O-{N-[2-{N-[2-(N,N-dimethylamino)ethyl]-N-methylamino}-ethyl]-N-methylaminocarbonyl]-3-L-phenyllactic acid Benzyl L-3-phenyllactate (7.7 g) was dissolved in tetrahydrofuran (100 mL) and carbonyl diimidazole (5.21 g) was added. The solution was stirred for 4 hours at room temperature, then $(CH_3)_2N\text{---}CH_2\text{---}CH_2\text{---}N(CH_3)\text{---}CH_2\text{---}CH_2\text{---}NHCH_3$ (4.9 g) was added. This mixture was stirred at room temperature for 48 hours, then the solvent was evaporated and the residue taken up in ethyl acetate. The organic layer was washed with brine, dried and evaporated to give the title compound as the corresponding benzyl ester. Debenzylation was effected by hydrogenolysis over 5% palladium-carbon at 60 psi and room temperature in ethanol to yield the title compound as a gummy solid; 300 MHz'H NMR: consistent with proposed structure.

Compounds of Formula I which can be prepared in accordance with the above-described general procedures are as follows:

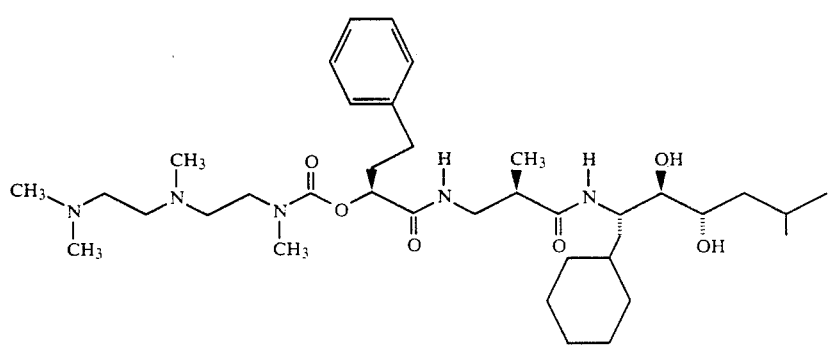

O-{N-[2-[2-(N,N-dimethylamino)ethyl]-N-methylamino}-ethyl]-N-methylaminocarbonyl}-3-L-homophenyllactyl-α-(R)-methyl-β-alanineamide of (2S,3R,4S)-2-amino-1-cyclohexyl-3,4-dihydroxy-6-methylheptane

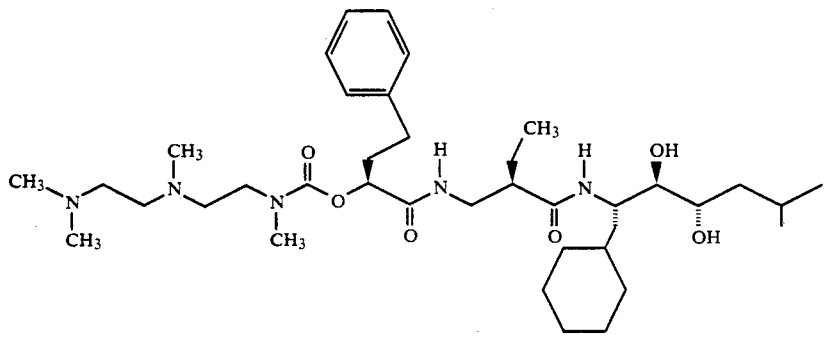

O-{N-[2-{N-[2-(N,N-dimethylamino)ethyl]-N-methylamino}-ethyl]-N-methylaminocarbonyl}-3-L-homophenyllactyl-α-(R)-ethyl-β-alanineamide of (2S,3R,4S)-2-amino-1-cyclohexyl-3,4-dihydroxy-6-methylheptane

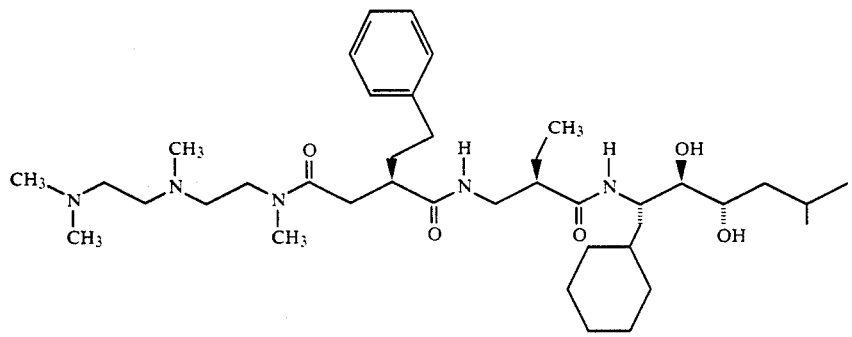

3-{N-[2-{N-[2-(N,N-dimethylamino)ethyl]-N-methylamino}-ethyl]-N-methylaminocarbonyl}-2-(R)-(2-phenylethyl)-propionyl-α-(R)-ethyl-β-alanineamide of (2S,3R,4S)-2-amino-1-cyclohexyl-3,4-dihydroxy-6-methylheptane

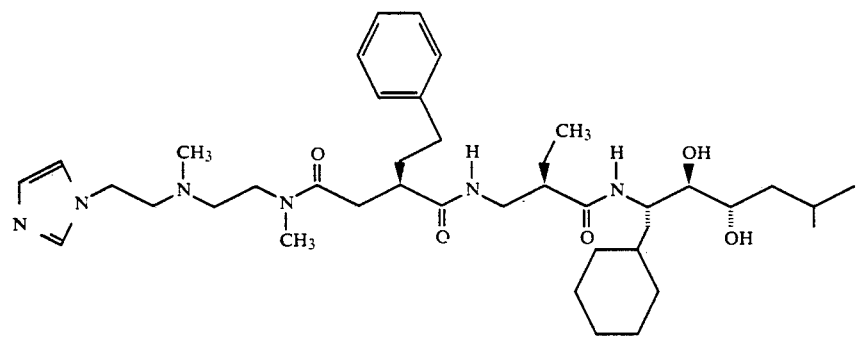

3{N-[2-{N-[2-(1-imidazole)ethyl]-N-methylamino}ethyl]-N-methylaminocarbonyl]-2-(R)-(2--phenylethyl)propionyl-α-(R)-ethyl-β-alanineamide of (2S,3R,4S)-2-amino-1-cyclohexyl-3,4-dihydroxy-6-methylheptane

BIOLOGICAL EVALUATION

Compounds of Formula I were evaluated as inhibitors of human renin in an in vitro assay, as follows: This human renin inhibition test has been previously described in detail [Papaioannou et al., Clinical and Experimental Hypertension, A7(9), 1243–1257 (1985)]. Human renin was obtained from the National Institute for Biological Standards, London. An incubation mixture was prepared containing in a total volume of 0.25 mL 100 mM Tris-acetate buffer at pH 7.4, $25 \times 10^{-6}$ Goldblatt units of renin, 0.05 mL of plasma from human volunteers taking oral contraceptives, 6.0 mM sodium EDTA, 2.4 mM phenylmethyl sulfonyl fluoride, 1.5 mM 8-hydroxyquinoline, 0.4 mg/mL BSA, and 0.024 mg/mL neomycin sulfate. This mixture was incubated for two hours at 37° C. in the presence or absence of renin inhibitors. The produced angiotensin I was determined by radioimmunoassay (New England Nuclear kit). Test compounds to be assayed were solubilized in DMSO and diluted with 100 mM Trisacetate buffer at pH 7.4 containing 0.5% bovine serum albumin (BSA) to the appropriate concentration. The final concentration of organic solvent in the reaction mixture was less than 1%. Control incubations at 37° C. were used to correct for effects of organic solvent on renin activity.

Biological Results:

TABLE I

In Vitro Effect of Compounds on Renin Activity

| Compound | Inhibition of Human Renin IC$_{50}$ |
|---|---|
| Example 10 | 2.4 nM |
| Example 11 | 1 nM |
| Example 12 | 110 nM |

The following is a description of a method for evaluation of the oral activity of compounds of Formula I as may be determined in vivo in Marmoset monkeys: Common marmosets (Callithrix jacchus, Charles River) are placed on a modified high protein low sodium diet (Purina, St. Louis, Mo.) for 1 to 2 weeks. On the day of the test an animal is anesthetized with isoflurane and cannulated in the femoral artery and vein for blood pressure monitoring, intravenous saralasin infusion and blood sampling. After allowing the animal to recover from surgery for 2 hr, saralasin is infused at 1 microgram/min for 15 minutes to confirm that the animal's blood pressure is dependent on angiotensin II levels. The marmoset is allowed to stabilize for 30 min after the saralasin infusion. The test compound is administered orally and blood pressure is monitored for 2 hr. Blood samples are taken in K-EDTA for plasma renin activity before, 30 min, and 1 hr after compound administration. It is expected that the specific compounds of Formula I, as described above, would exhibit oral activity by reducing plasma renin activity after one hour at a dose from 1 mg/kg up to 50 mg/kg body weight by a factor between about 50% and about 100%.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula

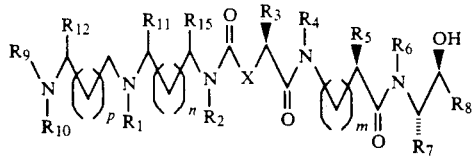

wherein X is selected from oxygen atom and methylene; wherein each of $R_9$ and $R_{10}$ is a group independently selected from hydrido methyl, ethyl, 2-(1H-imidazole-2-yl)ethyl and t-butyloxycarbonyl; wherein each of $R_1$ and $R_2$ is independently selected from hydrido, methyl, ethyl and isopropyl; wherein $R_3$ is selected from benzyl, phenethyl and cyclohexylmethyl; wherein each of $R_4$ and $R_6$ is hydrido; wherein $R_7$ is cyclohexylmethyl; wherein $R_8$ is isopropoxycarbonyl or 1-(S)-1-hydroxy-3-methylbut-1-yl; wherein each of $R_{11}$, $R_{12}$, $R_{14}$ and $R_{15}$ is hydrido; wherein m is zero or one and each of n and p is a number independently selected from zero through three; or a pharmaceutically-acceptable salt thereof; with the proviso that where m is zero, then $R_5$ is isobutyl; and with the further proviso that when m is one, then $R_5$ is methyl or ethyl.

2. Compound of claim 1 which is O-{N-[2-{N-[2-(N,N-dimethylamino)ethyl]-N-methylamino}-ethyl]-N-methylaminocarbonyl}-3-L-phenyllactyl-L-leucineamide of (2S,3R,4S)-2-amino-1-cyclohexyl-3,4-dihydroxy-6-methylheptane or a pharmaceutically-acceptable salt thereof.

3. Compound of claim 1 which is O-{N-[2-{N-[2-(N,N-dimethylamino)ethyl]-N-methylamino}-ethyl]-N-methylaminocarbonyl}-3-L-phenyllactyl-α-(R)-methyl-β-alanineamide of (2S,3R,4S)-2-amino-1-cyclohexyl-3,4-dihydroxy-6-methylheptane or a pharmaceutically-acceptable salt thereof.

4. Compound of claim 1 which is O-{N-[2-{N-[2-(N,N-dimethylamino)ethyl]-N-methylamino}-ethyl]-N-methylaminocarbonyl}-3L-homophenyllactyl-α-(R)-methyl-β-alanineamide of (2S,3R,4S)-2-amino-1-cyclohexyl-3,4-dihydroxy-6-methylheptane or a pharmaceutically-acceptable salt thereof.

5. Compound of claim 1 which is O-{N-[2-{N-[2-(N,N-dimethylamino)ethyl]-N-methylamino}-ethyl]-N-methylaminocarbonyl}-3L-homophenyllactyl-α-(R)-ethyl-β-alanineamide of (2R,3R,4S)-2-amino-1-cyclohexyl-3,4-dihydroxy-6-methylheptane or a pharmaceutically-acceptable salt thereof.

6. Compound of claim 1 which is 3-{N-[2-{N-[2-(N,N-dimethylamino)ethyl]-N-methylamino}-ethyl]-N-methylaminocarbonyl}-3(R)-(2-phenylethyl)-propionyl-α-(R)-ethyl-β-alanineamide of (2R,3R,4S)-2-amino-1-cyclohexyl-3,4-dihydroxy-6-methylheptane or a pharmaceutically-acceptable salt thereof.

7. Compound of claim 1 which is 3-{N-[2-(R)-(2-phenylethyl)-propionyl-α-(R)-ethyl-β-alanineamide of (2S,3R,4S)-2-amino-1-cyclohexyl-3,4-dihydroxy-6-methylheptane or a pharmaceutically-acceptable salt thereof.

8. A pharmaceutical composition comprising a therapeutically-effective amount of a renin-inhibiting compound and a pharmaceutically-acceptable carrier or diluent, said renin-inhibiting compound selected from a family of compounds of the formula

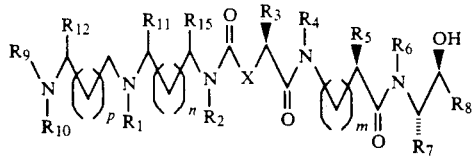

wherein X is selected from oxygen atom and methylene; wherein each of $R_9$ and $R_{10}$ is a group independently selected from hydrido methyl, ethyl, 2-(1H-imidazole-2-yl)ethyl and t-butyloxycarbonyl; wherein each of $R_1$ and $R_2$ is independently selected from hydrido, methyl, ethyl and isopropyl; wherein $R_3$ is selected from benzyl, phenethyl and cyclohexylmethyl; wherein each of $R_4$ and $R_6$ is hydrido; wherein $R_7$ is cyclohexylmethyl; wherein $R_8$ is isopropoxycarbonyl or 1-(S)-1-hydroxy-3-methylbut-1-yl; wherein each of $R_{11}$, $R_{12}$, $R_{14}$ and $R_{15}$ is hydrido; wherein m is zero or one of each of n and p is a number independently selected from zero through three; or a pharmaceutically-acceptable salt thereof; with the proviso that where m is zero, then $R_5$ is isobutyl; and with the further proviso that when m is one, then $R_5$ is methyl or ethyl.

9. The composition of claim 8 wherein said renin-inhibiting compound is O-{N-[2-{N-[2-(N,N-dimethylamino)ethyl]-N-methylamino}-ethyl]-N-methylaminocarbonyl}-3L-phenyllactyl-L-leucineamide of (2S,3R,4S)-2-amino-1-cyclohexyl-3,4-dihydroxy-6-methylheptane or a pharmaceutically-acceptable salt thereof.

10. The composition of claim 8 wherein said renin-inhibiting compound is O-{N-[2-{N-[2-(N,N-dimethylamino)ethyl]-N-methylamino}-ethyl]-N-methylaminocarbonyl}-3L-phenyllactyl-α-(R)-methyl-β-alanineamide of (2S,3R,4S)-2-amino-1-cyclohexyl-3,4-dihydroxy-6-methylheptane or a pharmaceutically-acceptable salt thereof.

11. The composition of claim 8 wherein said renin-inhibiting compound is O-{N-[2-{N-[2-(N,N-dimethylamino)ethyl]-N-methylamino}-ethyl]-N-methylaminocarbonyl}-3L-homophenyllactyl-α-(R)-methyl-β-alanineamide of (2S,3R,4S)-2-amino-1-cyclohexyl-3,4-dihydroxy-6-methylheptane or a pharmaceutically-acceptable salt thereof.

12. The composition of claim 8 wherein said renin-inhibiting compound is O-{N-[2-{N-[2-(N,N-dimethylamino)ethyl]-N-methylamino}-ethyl]-N-methylaminocarbonyl}-3L-homophenyllactyl-α-(R)-ethyl-β-alanineamide of (2S,3R,4S)-2-amino-1-cyclohexyl-3,4-dihydroxy-6-methylheptane or a pharmaceutically-acceptable salt thereof.

13. The composition of claim 8 wherein said renin-inhibiting compound is 3-{N-[2-(N,N-dimethylamino)ethyl]-N-methylamino}-ethyl]-N-methylaminocarbonyl}-2(R)-(2-phenylethyl)-propionyl-α-(R)-ethyl-β-alanineamide of (2S,3R,4S)-2-amino-1-cyclohexyl-3,4-dihydroxy-6-methylheptane or a pharmaceutically-acceptable salt thereof.

14. The composition of claim 8 wherein said renin-inhibiting compound is 3-{N-[2-{N-[2-(1-imidazole)ethyl]-N-methylamino}ethyl]-N-methylaminocarbonyl}-2-(R)-(2-phenylethyl)propionyl-α-(R)-ethyl-β-alanineamide of (2S,3R,4S)-2-amino-1-cyclohexyl-3,4-dihydroxy-6-methylheptane or a pharmaceutically-acceptable salt thereof.

15. A therapeutic method for treating hypertension, said method comprising administering to a hypertensive patient a therapeutically-effective amount of a compound of the formula

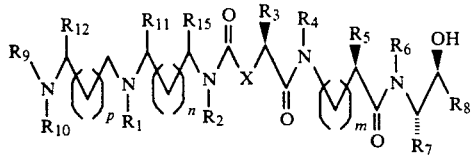

wherein X is selected from oxygen atom and methylene; wherein each of $R_9$ and $R_{10}$ is a group independently selected from hydrido methyl, ethyl, 2-(1H-imidazole-2-yl)ethyl and t-butyloxycarbonyl; wherein each of $R_1$ and $R_2$ is independently selected from hydrido, methyl, ethyl and isopropyl; wherein $R_3$ is selected from benzyl, phenethyl and cyclohexylmethyl; wherein each of $R_4$ and $R_6$ is hydrido; wherein $R_7$ is cyclohexylmethyl; wherein $R_8$ is isopropoxycarbonyl or 1-(S)-1-hydroxy-3-methylbut-1-yl; wherein each of $R_{11}$, $R_{12}$, $R_{14}$ and $R_{15}$ is hydrido; wherein m is zero or one of each of n and p is a number independently selected from zero through three; or a pharmaceutically-acceptable salt thereof; with the proviso that where m is zero, then $R_5$ is isobutyl; and with the further proviso that when m is one, then $R_5$ is methyl or ethyl.

16. The composition of claim 15 wherein said compound is O-{N-[2-{N-[2-(N,N-dimethylamino)ethyl]-N-methylamino}-ethyl]-N-methylaminocarbonyl}-3L-phenyllactyl-L-leucineamide of (2S,3R,4S)-2-amino-1-cyclohexyl-3,4-dihydroxy-6-methylheptane or a pharmaceutically-acceptable salt thereof.

17. The composition of claim 15 wherein said compound is O-{N-[2-{N-[2-(N,N-dimethylamino)ethyl]-N-methylamino}-ethyl]-N-methylaminocarbonyl}-3L-phenyllactyl-α-(R)-methyl-β-alanineamide of (2S,3R,4S)-2-amino-1-cyclohexyl-3,4-dihydroxy-6-methylheptane or a pharmaceutically-acceptable salt thereof.

18. The composition of claim 15 wherein said compound is O-{N-[2-{N-[2-(N,N-dimethylamino)ethyl]-N-methylamino}-ethyl]-N-methylaminocarbonyl}-3L-homophenyllactyl-α-(R)-methyl-β-alanineamide of (2S,3R,4S)-2-amino-1-cyclohexyl-3,4-dihydroxy-6-methylheptane or a pharmaceutically-acceptable salt thereof.

19. The composition of claim 15 wherein said compound is O-{N-[2-{N-[2-(N,N-dimethylamino)ethyl]-N-methylamino}-ethyl]-N-methylaminocarbonyl}-3L-homophenyllactyl-α-(R)-ethyl-β-alanineamide of (2S,3R,4S)-2-amino-1-cyclohexyl-3,4-dihydroxy-6-methylheptane or a pharmaceutically-acceptable salt thereof.

20. The composition of claim 15 wherein compound is 3-{N-[2-{N-[2-(N,N-dimethylamino)ethyl]-N-methylamino}-ethyl]-N-methylaminocarbonyl}-2(R)-(2-phenylethyl)-propionyl-α-(R)-ethyl-β-alanineamide of (2S,3R,4S)-2-amino-1-cyclohexyl-3,4-dihydroxy-6-methylheptane or a pharmaceutically-acceptable salt thereof.

21. The composition of claim 15 wherein said compound is 3-{N-[2-{N-[2-(1-imidazole)ethyl]-N-methylamino}ethyl]-N-methylaminocarbonyl}-2-(R)-(2-phenylethyl)propionyl-α-(R)-ethyl-β-alanineamide of (2S,3R,4S)-2-amino-1-cyclohexyl-3,4-dihydroxy-6-methylheptane or a pharmaceutically-acceptable salt thereof.

* * * * *